United States Patent
Donovan

(10) Patent No.: US 9,265,722 B2
(45) Date of Patent: Feb. 23, 2016

(54) BOTULINUM TOXIN FORMULATION FOR ORAL ADMINISTRATION

(75) Inventor: Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 939 days.

(21) Appl. No.: 11/779,121

(22) Filed: Jul. 17, 2007

(65) Prior Publication Data

US 2007/0269463 A1 Nov. 22, 2007

Related U.S. Application Data

(63) Continuation of application No. 10/288,906, filed on Nov. 5, 2002, now abandoned.

(51) Int. Cl.
| | |
|---|---|
| *A61K 38/48* | (2006.01) |
| *A61K 39/08* | (2006.01) |
| *A61K 9/00* | (2006.01) |
| *A61K 9/19* | (2006.01) |
| *A61K 9/16* | (2006.01) |
| *A61K 9/20* | (2006.01) |

(52) U.S. Cl.
CPC ............ *A61K 9/0065* (2013.01); *A61K 9/1647* (2013.01); *A61K 9/19* (2013.01); *A61K 9/204* (2013.01); *A61K 9/2018* (2013.01); *A61K 9/2063* (2013.01); *A61K 9/2068* (2013.01); *A61K 38/4893* (2013.01)

(58) Field of Classification Search
None
See application file for complete search history.

(56) References Cited

U.S. PATENT DOCUMENTS

| | | | |
|---|---|---|---|
| 3,523,906 A | | 8/1970 | Vrancken et al. |
| 3,691,090 A | | 9/1972 | Kitajima et al. |
| 3,737,337 A | | 6/1973 | Schnoring et al. |
| 3,773,919 A | | 11/1973 | Boswell et al. |
| 4,389,330 A | | 6/1983 | Tice et al. |
| 4,767,628 A | | 8/1988 | Hutchinson |
| 5,019,400 A | | 5/1991 | Gombotz et al. |
| 5,427,291 A | | 6/1995 | Smith |
| 5,437,291 A | | 8/1995 | Pasricha et al. |
| 5,601,848 A * | | 2/1997 | Marshall ............. 424/653 |
| 5,670,484 A | | 9/1997 | Binder |
| 5,674,205 A | | 10/1997 | Pasricha et al. |
| 5,696,077 A * | | 12/1997 | Johnson et al. ............. 514/2 |
| 5,714,468 A | | 2/1998 | Binder |
| 5,766,605 A | | 6/1998 | Sanders et al. |
| 5,902,565 A | | 5/1999 | Cox et al. ............. 424/1.29 |
| 5,989,545 A | | 11/1999 | Foster et al. |
| 6,051,239 A | | 4/2000 | Simpson et al. ........... 424/239.1 |
| 6,063,768 A | | 5/2000 | First |
| 6,113,915 A | | 9/2000 | Aoki et al. |
| 6,139,845 A | | 10/2000 | Donovan |
| 6,143,306 A | | 11/2000 | Donovan |
| 6,265,379 B1 | | 7/2001 | Donovan |
| 6,299,893 B1 | | 10/2001 | Schwartz et al. |
| 6,306,403 B1 | | 10/2001 | Donovan |
| 6,306,423 B1 | | 10/2001 | Donovan et al. ............. 424/423 |
| 6,312,708 B1 | | 11/2001 | Donovan |
| 6,328,977 B1 | | 12/2001 | Donovan |
| 6,358,513 B1 | | 3/2002 | Voet et al. |
| 6,358,917 B1 * | | 3/2002 | Carruthers et al. ............. 514/2 |
| 6,365,164 B1 | | 4/2002 | Schmidt |
| 6,383,509 B1 | | 5/2002 | Donovan et al. ............. 424/423 |
| 6,395,277 B1 | | 5/2002 | Graham |
| 6,423,319 B1 | | 7/2002 | Brooks et al. |
| 6,458,365 B1 | | 10/2002 | Aoki et al. |
| 6,464,986 B1 | | 10/2002 | Aoki et al. |
| 6,506,399 B2 | | 1/2003 | Donovan ............. 424/423 |
| 6,585,993 B2 | | 7/2003 | Donovan et al. ............. 424/423 |
| 6,669,962 B2 | | 12/2003 | Fanta et al. ............. 424/490 |
| 6,773,711 B2 | | 8/2004 | Voet et al. ............. 424/239.1 |
| 6,787,517 B1 * | | 9/2004 | Gil et al. ............. 514/1 |
| 6,849,271 B2 | | 2/2005 | Vaghefi et al. ............. 424/459 |
| 8,017,131 B2 * | | 9/2011 | Donovan ............. 424/239.1 |
| 8,409,828 B2 * | | 4/2013 | Xiang et al. ............. 435/71.1 |
| 2002/0028244 A1 | | 3/2002 | Donovan et al. ............. 424/486 |
| 2004/0028703 A1 | | 2/2004 | Bigalke et al. ............. 424/239.1 |
| 2008/0160121 A1* | | 7/2008 | Donovan et al. ............. 424/780 |
| 2012/0238504 A1* | | 9/2012 | Moyer et al. ............. 514/18.1 |

FOREIGN PATENT DOCUMENTS

| | | |
|---|---|---|
| EP | 0 605 501 B1 | 4/1999 |
| WO | WO 95/17904 | 7/1995 |

OTHER PUBLICATIONS

Li et al (Sichuan Daxue Xuebae (Ziran Kexueban, Apr. 2000, vol. 37, No. 2, p. 238-241), (Abstract 1)(Abstract only).*
Qui et al (Sichuan Daxue Xuebae (Ziran Kexueban, Apr. 2000, vol. 37, No. 2, p. 238-2410,(Abstract 2)Abstract only).*
Mandel et al (Eur J Gastroentrol Heptal, May 2001; 13(5):603-9).*
Hunter et al (Am J Obstet Gynecol, vol. 185, No. 5, p. 1174-1179, 2001).*
Wenli et al (Sichuan Daxue Xuebae (Ziran Kexueban, Apr. 2000, vol. 37, No. 2, p. 238-241)(Abstract only).*
Wang et al (Journal of Controlled Release 73 (2001) 223-231).*
Qui et al (Sichuan Daxue Xuebae (Ziran Kexueban, Apr. 2000, vol. 37, No. 2, p. 238-241)(Abstract only).*
Albanese, A., et al., *The use of botulinum toxin on smooth muscles*, Eur J. Neurol Nov. 1995; 2(supp 3): 29-33.
Aoki, K.R., 1999, *Preclinical Update on BOTOX® (Botulinum Toxin Type A)—Purified Neurotoxin Complex Relative to Other Botulinum Neurotoxin Preparations*, European J. Neurology v6 (suppl 4), pp. S3-S10.
Bigalke, H., et al., *Botulinum A Neurotoxin inhibits non-cholinergic synaptic transmission in mouse spinal cord neurons in culture*, Brain Res 1985; 360: 318-324.
Bigalke, H., et al., *Tetanus toxin and botulinum A toxin inhibit release and uptake of various transmitters, as studied with particulate preparations from rat brain and spinal cord*, Naunyn Schmiedebergs Arch Pharmacol 1981; 316:244-51.

(Continued)

*Primary Examiner* — Nita M Minnifield
(74) *Attorney, Agent, or Firm* — Brigitte C. Phan

(57) ABSTRACT

Pharmaceutical compositions of a botulinum toxin for oral administration to a patient with a gastrointestinal disorder.

3 Claims, No Drawings

(56) References Cited

OTHER PUBLICATIONS

Binz, T., et al., *The complete sequence of botulinum neurotoxin type A and comparison with other clostridial neurotoxins*, y and Molecular Biology, Inc., vol. 265, No. 16, Jun. 5, 1990, pp. 9153-9158.

Boyd, R.S., et al., *The effect of botulinum neurotoxin-B on insulin release from a β-cell line*, Mov Disord May 1995;10(3):376.

Boyd, R.S., et al., *The insulin secreting β-cell line, HIT-15, contains SNAP-25 which is a target for botulinum neurotoxin-A*, Mov Disord May 1995; 10(3):376.

Coffield, J.A., et al., p. 5, *The site and mechanism of action of botulinum neurotoxin*, Therapy with Botulinum Toxin, 1994, Ed. J. Jankovic, et al., Marcel Dekker, Inc. publisher.

Crowell, M.D., et al., *Botulinum Toxin reduces pyloric dysfunction in patients with diabetic gastroparesis*, Gastroenterology Apr. 2002; 122(4 Supp 1): A451-A452 (1 page).

Dykstra, D., et al., *Treatment of detrusor-sphincter dyssynergia with botulinum A toxin: a double blind study*, Arch Phys Med Rehabil Jan. 1990;71:24-26.

Eaker, E.Y, et al., *Untoward effects of esophageal botulinum toxin injection in the treatment of achalasia*, Dig Dis Sci Apr. 1997:42(4):724-7.

Gonelle-Gispert, C., et al., *Snap-25a and -25b isoforms are both expressed in insulin-secreting cells and can function in insulin secretion; Biochem J.* (1999) 339, )pt 1): 159-165.

Gui, D. et al., *Effects of botulinum toxin on gastric emptying and digestive secretions. A possible tool for correction of obesity*, Naunyn Schmiedebergs Arch Pharmacol Jun. 2002:365(Suppl 2):R22.

Gui, D., et al., *Botulinum toxin injected in the gastric wall reduces body weight and food intake in rats*, Aliment Pharmacol Ther Jun. 2000:14(6):829-834.

Habermann, E., et al., *Tetanus toxin and botulinum A and C neurotoxins inhibit noradrenaline release from cultured mouse brain.* Journal of Neurochemistry, 51,522-527, 1988.

Habermann, E., *I-labeled Neurotoxin from clostridium botulinum A: preparation, binding to synaptosomes and ascent to the spinal cord*, Naunyn Schmiedebergs Arch Pharmacol 1974; 281:47-56.

Habermann, E., *Inhibition by tetanus and botulinum A toxin of the release of [3H]noradrenaline and [3H]GABA from rate brain homogenate*, Experientia Mar. 15, 1988;44(3):224-6.

Hanson, M.A., et al., *Structural view of botulinum neurotoxin in numerous functional states*, Scientific and therapeutic aspects of botulinum toxin, 2002, ed. M. Brin, et al., Pub.—Lippincott Williams & Wilkins.

Harrison's principles of internal medicine, 14th Edition, ed. By Fauci, et al., (1998).

Hoogerwerf, W., et al., *Botulinum toxin for spastic gastrointestinal disorders*, Bailliere's Clin Gastroenterol 1999;13(1):131-143.

Johnson, E.A., 1999, *Clostridial Toxins as Therapeutic Agents: Benefits of Nature's Most Toxic Proteins*, Annu. Rev. Microbiol. V53, pp. 551-575.

Kohl, A., et al., *Comparison of the effect of botulinum toxin A (Botox®) with the high-purified neurotoxin (NT 201) in the extensor digitorum brevis muscle test*, MovDisord 2000;15(suppl 3):165.

Kondo, T., et al., *Modificaton of the action of pentagastrin on acid secretion by botulinum toxin*, Experientia 1977;33:750-1.

Langer, Robert; New Methods of Drug Delivery; *Science*, vol. 249; Sep. 28, 1990; pp. 1527-1533.

Laskawi, R., et al., *Up-to-date report of botulinum toxin type A treatment in patients with gustatory sweating (Frey's Syndrome)*, Laryngoscope Mar. 1998;108(3):381-4.

Mandel et al., Eur. J. Gstroenterol Heptal, May 2001, 13(5), pp. 603-609.

Marjama-Lyons, J., et al., *Tremor-predominant Parkinson's disease*, Drugs & Aging Apr. 2000; 16(4):273-278.

Meyer, K.E., *A comparative systemic toxicity study of neurobloc in adult and juvenile cynomolgus monkeys*, Mov Disord 2000;15(Suppl 2):54.

Moyer, E., *Botulinum toxin type B: experimental and clinical experience*, Neurological Disease and Therapy. Therapy with botulinum toxin. New York, Marcel Dekker; 1994;25pp. 71-85.

Naumann, M., et al., *Botulinum toxin type A in the treatment of focal, axillary and palmar hyperhidrosis and other hyperhidrotic conditions*, Euro. J. Neurology, 1999, 6 suppl 4:S111-S115.

Ohishi, I., et al., 1997, *Oral Toxcities of Clostridium Botulinum Toxins in Response to Molecular Size*, Infection and Immunity, Apr. 1977, v16(1), pp. 107-109.

Pearce, L. B. , et al., *Pharmacologic characterization of botulinum toxin for basic science and medicine*, Toxicon 1997;35(9):1373-412.

Qui et al., Sichuan Daxue Xhuebae, Ziran Kexueban, Apr. 2000, vol. 37, No. 2, pp. 238-241 (Abstract only).

Ragona, R., et al., *Management of parotid sialocele with botulinum toxin*, Laryngoscope Aug. 1999;109(8):1344-1346.

Rossi, S., et al., *Immunohistochemical localization of SNAP-25 protein in the stomach of rat*, Naunyn Schmiedebergs Arch Pharmacol, 2002;365(suppl 2):R37.

Sanchez-Prieto, J., *Botulinum toxin A blocks glutamate exocytosis from guinea-pig cerebral cortical synaptosomes*, Eur J Biochem Jun. 1987;165(3):675-81.

Schantz, E.J., et al., *Preparation and characterization of botulinum toxin type A for human treatment*, Chap 3, pp. 41-49, Therapy with Botulinum Toxin, 1994, Ed. J. Jankovic, et al., Marcel Dekker, Inc. publisher.

Schantz, E.J., et al., *Properties and use of botulinum toxin and other microbial neurotoxins in medicine*, Microbiol Rev Mar. 1992;56(1):80-99.

Schwendeman, Steven, et al.; Peptide, Protein, and Vaccine Delivery from Implantable Polymeric Systems; *Controlled Drug Delivery Challenges and Strategies*, Chapter 12; American Chemical Society, 1997; pp. 229-267.

Singh, Bal Ram; Critical Aspects of Bacterial Protein Toxins; *Natural Toxins II*, ed by B. R. Singh, et al,; Plenum Press, New York, 1996; pp. 63-84.

Sinha, Vivek R., et al.; Bioabsorbable Polymers for Implantable Therapeutic Systems; *Drug Development and Industrial Pharmacy*, 24 (12), 1998; pp. 1129-1138.

Sloop, R.R., et al., *Reconstituted botulinum toxin type A does not lose potency in humans if it is refrozen or refrigerated for 2 weeks before use*, Neurology Jan. 1997;48(1):249-53.

Takeuchi, Hirofumi, et al.; Mucoadhesive nanoparticulate systems for peptide drug delivery; *Advanced drug Delivery Reviews* 47 (2001); pp. 39-54.

Veronese, F.M.; Polyorganophosphazene micropheres for drug release: polymer synthesis, microsphere preparation, in vitro and in vivo naproxen release; *Journal of Controlled Release*; 52 (1998); pp. 227-237.

Wang et al., Journal of Controlled Release 73, 2001, pp. 223-231.

Wang, Z, et al., *Effects of botulinum toxin on gastric myoelectrical and vagal activities in dogs*, Gastroenterology Apr. 2001; 120 (5 Suppl 1):A-718.

Wiegand, H., et al., *I-Labelled botulinum A neurotoxin pharmacokinetics in cats after intramuscular injection.* Naunyn Schmiedebergs Arch Pharmacol, 1976;292:161-5.

Wiesel, P.H., et al., *Botulinum toxin for refractory postoperative pyloric spasm*, Endoscopy 1997;29(2):132.

Woodley, John; Bioadhesion: New Possibilities for Drug Administration; Clinical Pharmacokinetic 2001; 40 (2) pp. 77-84.

Botox Type A, Information Sheet, 2000, p. 1-9.

Botox Type B, Information Sheet, 2000, p. 1-16.

Lew, M.F., Analysis of the Duration of Efficacy of Botulinum Toxin Type B in Patients with Cervical Dystonia, Mov Disord Sep. 2002; 17(5):1142.

Moberg-Wolff, E., Welke, K., *Use of botulinum toxin type B in the pediatric population*, Arch Phys Med Rehabil Mar. 2002,83(11):1673 ABS—Poster 173.

\* cited by examiner

BOTULINUM TOXIN FORMULATION FOR ORAL ADMINISTRATION

CROSS REFERENCE

This application is a continuation of pending application Ser. No. 10/288,906, filed Nov. 5, 2002. The entirety of this prior application is incorporated herein by reference.

BACKGROUND

The present invention relates to pharmaceutical compositions. In particular, the present invention relates to pharmaceutical compositions of a botulinum toxin for oral administration.

A pharmaceutical composition can be formulated for oral, intravenous, intramuscular, subcutaneous, or inhalation administration as well as by other routes (i.e. enema, intranasal, intrathecal, etc). Advantages of orally administered pharmaceuticals (as a solution, suspension, tablet, capsule, etc) include rapid therapeutic effect and patient convenience.

It is know to orally administer a pharmaceutical for direct effect on a target site within the gastrointestinal tract, as opposed to a therapeutic effect by the active ingredient of the pharmaceutical composition upon absorption into the patient's circulatory system (i.e. antacids, laxatives). The controlled gastric retention of solid dosage forms of a pharmaceutical can be achieved by the mechanisms of mucoadhesion, flotation, sedimentation, expansion, or by the simultaneous administration of pharmacological agents which delay gastric emptying.

Mucoadhesion is the process whereby synthetic and natural macromolecules adhere to mucosal surfaces in the body. If these materials are then incorporated into pharmaceutical formulations, drug absorption by mucosal cells can be enhanced or the drug released at the site for an extended period of time. For synthetic polymers, such as the chitosans, carbopols and carbomers, the mechanism of bio/mucoadhesion is the result of a number of different physicochemical interactions. Biological bio/mucoadhesives, such as plant lectins, show specific interactions with cell surfaces and mucin and are seen as the 'second generation' bioadhesives. Woodley, J., *Bioadhesion: new possibilities for drug administration?*, Clin Pharmacokinet 2001; 40(2):77-84. Thus, mucoadhesion acts to impart to orally administered dosage forms the ability to resist the strong propulsion forces of the stomach wall. The continuous production of mucous by the gastric mucosa to replace the mucous which is lost through the peristaltic contractions and the dilution of the stomach content can be overcome by use of mucoadhesion as a gastroretentive force.

Mucoadhesive nanoparticulate systems, including liposomes and polymeric nanoparticles, have been evaluated. Mucoadhesive ability can be conferred on particulate systems by coating their surface with mucoadhesive polymers such as chitosan and Carbopol. The feasibility of such surface modification has been confirmed by measuring the zeta potential. Evaluation procedures include a particle counting method using a Coulter counter for polymer-coated liposomes. Mucoadhesive nanoparticles have been used for the oral administration of peptide drugs, and have been shown to be more effective with a more prolonged action as compared to non-coated systems. Takeuchi H., et al, *Mucoadhesive nanoparticulate systems for peptide drug delivery*, Adv Drug Deliv Rev 2001 Mar. 23; 47(1):39-54.

Mucoadhesive drug delivery devices offer several advantages over traditional dosage forms including the ability to optimize the therapeutic effects of a drug by controlling its release into the body. It has been shown that various types of poly(acrylic acid) (PAA) hydrogels are able to inhibit the hydrolytic activity of gastrointestinal enzymes, such as trypsin, resulting in an increase of the bioavailability of the drug. Acrylic-based polymers can be used for the attachment of mucoadhesive delivery systems to the mucosa. Polymer hydrogels modified by grafting mucophilic copolymers such as poly(ethylene glycol) (PEG) onto the back-bone chains of the polymer can promote the adhesive process. This is due to the ability of these grafted chains to diffuse from the network to the mucous layer. Films of P(AA-g-EG) can be synthesized by using UV-initiated free-radical solution polymerization. Different types of hydrogels can be synthesized with varying molar feed ratio of AA to PEG. The polymer hydrogels are characterized by mucoadhesion in order to quantify the effects of the PEG grafted chains on mucoadhesion. The bioadhesive bond strength can be determined using a tensile apparatus, and the work of adhesion thereby calculated. Hydrogels containing 40% AA and 60% PEG (40:60 AA/EG) can exhibit the highest mucoadhesion. These results can be attributed to the synergistic effects of both monomers. AA functional groups can permit the polymer to form multiple hydrogen bonds as well as to swell to a large degree. PEG tethers acted as mucoadhesive promoters. They penetrated into the mucosa and bridged the base hydrogel and the mucus. These results can also be interpreted in terms of the recent Huang-Peppas models (2002) of surface coverage and chain length effects in mucoadhesion.

Flotation as a retention mechanism requires the presence of liquid on which the dosage form can float, and it also presumes that the patient remains in an upright posture during the GRI, because in a supine position the pylorus is located above the stomach body and allows the accelerated emptying of floating material. Thus, flotation can be a basis principle for gastric retention of an oral formulation.

Sedimentation has been successfully used as a retention mechanism for pellets which are small enough to be retained in the rugae or folds of the stomach body near the pyloric region, which is the part of the organ with the lowest position in an upright posture. Dense pellets (approx. 3 g/cm$^3$) trapped in rugae also tend to withstand the peristaltic movements of the stomach wall. Expansion has been shown to be a potentially reliable retention mechanism. Several devices with features which extend, unfold or which are inflated by carbon dioxide generated in the devices after administration have been described. These dosage forms are excluded from the passage of the pyloric sphincter if they exceed a diameter of approx. 12-18 mm in their expanded state. Various mechanisms ensure the full reversibility of the expansion.

Gastrointestinal disorders treatable by an orally administered pharmaceutical composition can include abnormal bowel function, abdominal distention, constipation, Cohn's disease, diarrhea, fat malabsorption, food allergies, gastrointestinal fistula, glucose Intolerance, gluten Intolerance, impaired digestion and absorption, lactose intolerance, limited gut function, malabsorption syndrome, pancreatic disorders, short bowel syndrome, volume intolerance, vomiting, nausea, heartburn, appendicitis, diverticular disease, gallstones, gastrointestinal reflux, inflammatory disease, peptic ulcers, hemorrhoids, hernia and obesity Gastrointestinal motility can be defined by the movements of the digestive system, and the transit of the contents within it. When nerves or muscles in any portion of the digestive tract do not function in a strong coordinated fashion, a person develops symptoms related to motility problems. These symptoms may range from heartburn to constipation. Other symptoms may also include abdominal distention, nausea, vomiting, and diarrhea.

An oral formulation can made so as to deliver a pharmaceutical to the GI tract at a predetermined rate over a specific time period. Generally, the release rate of a drug from an oral formulation is a function of the physiochemical properties of the oral formulation material and incorporated drug. Typically, an oral formulation includes a carrier made of an inert material which elicits little or no host response.

An oral formulation can comprise a drug with a biological activity incorporated into a carrier material. The carrier can be a polymer or a bioceramic material. The oral formulation can be swallowed to release a drug in a manner and amount which can impart a desired therapeutic efficacy.

Polymeric carrier materials can release drugs due to diffusion, chemical reaction or solvent activation, as well as upon influence by magnetic, ultrasound or temperature change factors. Diffusion can be from a reservoir or matrix. Chemical control can be due to polymer degradation or cleavage of the drug from the polymer. Solvent activation can involve swelling of the polymer or an osmotic effect. See e.g. *Science* 249; 1527-1533:1990.

A membrane or reservoir oral formulation depends upon the diffusion of a bioactive agent across a polymer membrane. A matrix oral formulation is comprised of a polymeric matrix in which the bioactive agent is uniformly distributed. Swelling-controlled release systems are usually based on hydrophilic, glassy polymers which undergo swelling in the presence of biological fluids or in the presence of certain environmental stimuli.

An oral formulation can comprise a carrier which is substantially non-toxic, non-carcinogenic, and non-immunogenic. Suitable oral formulation materials can include polymers such as poly(2-hydroxy ethyl methacrylate) (p-HEMA), poly(N-vinyl pyrrolidone) (p-NVP)+, poly(vinyl alcohol) (PVA), poly(acrylic acid) (PAA), polydimethyl siloxanes (PDMS), ethylene-vinyl acetate copolymers (EVAc), polyvinylpyrrolidone/methylacrylate copolymers, poly(lactic acid) (PLA), poly(glycolic acid) (PGA), polyanhydrides, poly (ortho esters), collagen and cellulosic derivatives and bioceramics, such as hydroxyapatite (HPA), tricalcium phosphate (TCP), and aliminocalcium phosphate (ALCAP). Lactic acid, glycolic acid, collagen and copolymers thereof can be used to make biodegradable oral formulations.

Biodegradable oral formulations can be used to overcome the evident deficiencies of nonbiodegradable oral formulations. See, e.g., U.S. Pat. Nos. 3,773,919 and 4,767,628. A biodegradable polymer can be a surface eroding polymer, as opposed to a polymer which displays bulk or homogenous degradation. A surface eroding polymer degrades only from its exterior surface, and drug release is therefore proportional to the polymer erosion rate. A suitable such polymer can be a polyanhydride. An oral formulation can be in the form of solid cylindrical oral formulations, pellet microcapsules, or microspheres. *Drug Development and Industrial Pharmacy* 24(12); 1129-1138:1998. A biodegradable oral formulation can be based upon either a membrane or matrix release of the bioactive substance. Biodegradable microspheres for oral administration can be formulated by being pressed into a disc or pellet.

An oral formulation can be made of a biodegradable materials, such as polymers of polylactic acid (PLA), polyglycolic acid (PGA) polylactic acid-glycolic acid copolymers, polycaprolactones and cholesterol are known.

A least three methods for preparing polymeric microspheres, including microspheres composed of a biodegradable polymer, are known. See e.g. *Journal of Controlled Release* 52(3); 227-237:1998. Thus, a solid drug preparation can be dispersed into a continuous phase consisting of a biodegradable polymer in an organic solvent or, an aqueous solution of a drug can be emulsified into the polymer-organic phase. Microspheres can then be formed by spray-drying, phase separation or double emulsion techniques.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyamide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1996) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with Available from Allergan, Inc., of Irvine, Calif. under the tradename BOTOX® in 100 1unit vials high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Gonelle-Gispert, C., et al., *SNAP-25a and -25b isoforms are both expressed in insulin-secreting cells and can function in insulin secretion*, Biochem J. 1; 339 (pt 1):159-65:1999, and Boyd R. S. et al., *The effect of botulinum neurotoxin-B on insulin release from a ∃-cell line*, and Boyd R. S. et al., *The insulin secreting ∃-cell line, HIT-15, contains SNAP-25 which is a target for botulinum neurotoxin-A*, both published at *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for a lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy.

Botulinum toxins and toxin complexes can be obtained from, for example, List Biological Laboratories, Inc., Campbell, Calif.; the Centre for Applied Microbiology and Research, Porton Down, U.K.; Wako (Osaka, Japan), as well as from Sigma Chemicals of St Louis, Mo. Commercially available botulinum toxin containing pharmaceutical compositions include BOTOX® (Botulinum toxin type A neurotoxin complex with human serum albumin and sodium chloride) available from Allergan, Inc., of Irvine, Calif. in 100 unit vials as a lyophilized powder to be reconstituted with 0.9% sodium chloride before use), Dysport® (*Clostridium botulinum* type A toxin haemagglutinin complex with human serum albumin and lactose in the formulation), available from Ipsen Limited, Berkshire, U.K. as a powder to be reconstituted with 0.9% sodium chloride before use), and MyoBloc™ (an injectable solution comprising botulinum toxin type B, human serum albumin, sodium succinate, and sodium chloride at about pH 5.6, available from Elan Corporation, Dublin, Ireland).

The success of botulinum toxin type A to treat a variety of clinical conditions has led to interest in other botulinum toxin serotypes. Additionally, pure botulinum toxin has been used to treat humans. See e.g. Kohl A., et al., *Comparison of the effect of botulinum toxin A (Botox (R)) with the highly-purified neurotoxin (NT 201) in the extensor digitorum brevis muscle test*, Mov Disord 2000; 15(Suppl 3):165. Hence, a pharmaceutical composition can be prepared using a pure botulinum toxin.

The type A botulinum toxin is known to be soluble in dilute aqueous solutions at pH 4-6.8. At pH above about 7 the stabilizing nontoxic proteins dissociate from the neurotoxin, resulting in a gradual loss of toxicity, particularly as the pH and temperature rise. Schantz E. J., et al *Preparation and characterization of botulinum toxin type A for human treatment* (in particular pages 44-45), being chapter 3 of Jankovic, J., et al, *Therapy with Botulinum Toxin*, Marcel Dekker, Inc (1994).

The botulinum toxin molecule (about 150 kDa), as well as the botulinum toxin complexes (about 300-900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1987. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [$^3$H]Noradrenaline and [$^3$H]GABA From Rat Brain Homogenate*, Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3\times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, Properties and use of Botulinum toxin and Other Microbial Neurotoxins in Medicine, Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2\times 10^8$ $LD_{50}$ U/mg or greater; purified botulinum toxin type B with an approximately 156 kD molecular weight with a specific potency of $1-2\times 10^8$ $LD_{50}$ U/mg or greater, and; purified botulinum toxin type F with an approximately 155 kD molecular weight with a specific potency of $1-2\times 10^7$ $LD_{50}$ U/mg or greater.

Either the pure botulinum toxin (i.e. the 150 kilodalton botulinum toxin molecule) or the toxin complex can be used to prepare a pharmaceutical composition. Both molecule and complex are susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249-53:1997.

Botulinum toxins have been used in clinical settings for the treatment of neuromuscular disorders characterized by hyperactive skeletal muscles. Botulinum toxin type A (Botox®) was approved by the U.S. Food and Drug Administration in 1989 for the treatment of essential blepharospasm, strabismus and hemifacial spasm in patients over the age of twelve. In 2000 the FDA approved commercial preparations of type A (Botox®) and type B botulinum toxin (MyoBloc™) serotypes for the treatment of cervical dystonia, and in 2002 the FDA approved a type A botulinum toxin (Botox®) for the cosmetic treatment of certain hyperkinetic (glabellar) facial wrinkles. Clinical effects of peripheral intramuscular botulinum toxin type A are usually seen within one week of injection and sometimes within a few hours. The typical duration of symptomatic relief (i.e. flaccid muscle paralysis) from a single intramuscular injection of botulinum toxin type A can be about three months, although in some cases the effects of a botulinum toxin induced denervation of a gland, such as a salivary gland, have been reported to last for several years. For example, it is known that botulinum toxin type A can have an efficacy for up to 12 months (Naumann M., et al., *Botulinum toxin type A in the treatment of focal, axillary and palmar hyperhidrosis and other hyperhidrotic conditions*, European J. Neurology 6 (Supp 4): S111-S115:1999), and in some circumstances for as long as 27 months. Ragona, R. M., et al., *Management of parotid sialocele with botulinum toxin*, The Laryngoscope 109:1344-1346:1999. However, the usual duration of an intramuscular injection of Botox® is typically about 3 to 4 months.

It has been reported that a botulinum toxin type A has been used in diverse clinical settings, including for example as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
  (a) flexor digitorum profundus: 7.5 U to 30 U
  (b) flexor digitorum sublimus: 7.5 U to 30 U
  (c) flexor carpi ulnaris: 10 U to 40 U
  (d) flexor carpi radialis: 15 U to 60 U
  (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Lyons, J., et al., *Tremor-Predominant Parkinson's Disease*, Drugs & Aging 16(4); 273-278:2000.

Treatment of certain gastrointestinal and smooth muscle disorders with a botulinum toxin are known. See e.g. U.S. Pat. Nos. 5,427,291 and 5,674,205 (Pasricha). Additionally, transurethral injection of a botulinum toxin into a bladder sphincter to treat a urination disorder is known (see e.g. Dykstra, D. D., et al, *Treatment of detrusor-sphincter dyssynergia with botulinum A toxin: A double-blind study*, Arch Phys Med Rehabil 1990 January; 71:24-6), as is injection of a botulinum toxin into the prostate to treat prostatic hyperplasia. See e.g. U.S. Pat. No. 6,365,164 (Schmidt).

U.S. Pat. No. 5,766,605 (Sanders) proposes the treatment of various autonomic disorders, such as hypersalivation and rhinittis, with a botulinum toxin.

Furthermore, various afflictions, such as hyperhydrosis and headache, treatable with a botulinum toxin are discussed in WO 95/17904 (PCT/US94/14717) (Aoki). EP 0 605 501 B1 (Graham) discusses treatment of cerebral palsy with a botulinum toxin and U.S. Pat. No. 6,063,768 (First) discusses treatment of neurogenic inflammation with a botulinum toxin.

In addition to having pharmacologic actions at the peripheral location, botulinum toxins can also have inhibitory effects in the central nervous system. Work by Weigand et al, ($^{125}$*I-labelled botulinum A neurotoxin: pharmacokinetics in cats after intramuscular injection*, Nauny-Schmiedeberg's Arch. Pharmacol. 1976; 292, 161-165), and Habermann, ($^{125}$*I-labelled Neurotoxin from clostridium botulinum A: preparation, binding to synaptosomes and ascent to the spi-* nal cord, Nauny-Schmiedeberg's Arch. Pharmacol. 1974; 281, 47-56) showed that botulinum toxin is able to ascend to the spinal area by retrograde transport. As such, a botulinum toxin injected at a peripheral location, for example intramuscularly, may be retrograde transported to the spinal cord.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

A botulinum toxin has also been proposed for the treatment of hyperhydrosis (excessive sweating, U.S. Pat. No. 5,766, 605), headache, (U.S. Pat. No. 6,458,365, migraine headache (U.S. Pat. No. 5,714,468), post-operative pain and visceral pain (U.S. Pat. No. 6,464,986), pain by intraspinal administration (U.S. Pat. No. 6,113,915), Parkinson's disease by intracranial administration (U.S. Pat. No. 6,306,403), hair growth and hair retention (U.S. Pat. No. 6,299,893), psoriasis and dermatitis (U.S. Pat. No. 5,670,484), injured muscles (U.S. Pat. No. 6,423,319, various cancers (U.S. Pat. No. 6,139,845), pancreatic disorders (U.S. Pat. No. 6,143,306), smooth muscle disorders (U.S. Pat. No. 5,437,291, including injection of a botulinum toxin into the upper and lower esophageal, pyloric and anal sphincters)), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977). Additionally, controlled release toxin implants are known (U.S. Pat. Nos. 6,306,423 and 6,312,708).

It has been reported that that intravenous injection of a botulinum toxin causes a decline of pentagastrin stimulated acid and pepsin secretion in rats. Kondo T., et al., *Modification of the action of pentagastrin on acid secretion by botulinum toxin*, Experientia 1977; 33:750-1. Additionally it has been speculated that a botulinum toxin can be used to reduce a gastrointestinal secretion, such as a gastric secretion. See pages 16-17 of WO 95/17904. Furthermore, a botulinum toxin has been proposed for the treatment of disorders of gastrointestinal muscle in the enteric nervous system disorder (U.S. Pat. No. 5,437,291) and well as to treat various autonomic disorders (U.S. Pat. No. 5,766,605). Botulinum toxin has been injected into the fundus of the stomach of dogs. Wang Z., et al., *Effects of botulinum toxin on gastric myoelectrical and vagal activities in dogs*, Gastroenterology 2001 April; 120(5 Suppl 1):A-718. Additionally, intramuscular injection of a botulinum toxin into the gastric antrum has been proposed as a treatment for obesity. See e.g. Gui D., et al., *Effects of botulinum toxin on gastric emptying and digestive secretions. A possible tool for correction of obesity*?, Naunyn Schmiedebergs Arch Pharmacol 2002 June; 365(Suppl 2):R22; Albanese A., et al., *The use of botulinum toxin on smooth muscles*, Eur J Neurol 1995 November; 2(Supp 3):29-33, and; Gui D., et al., *Botulinum toxin injected in the gastric wall reduces body weight and food intake in rats*, Aliment Pharmacol Ther 2000 June; 14(6):829-834. Furthermore, botulinum toxin type A has been proposed as a therapeutic application for the control of secretion in the stomach. Rossi S., et al., *Immunohistochemical localization of SNAP-25 protein in the stomach of rat*, Naunyn Schmiedebergs Arch Pharmacol 2002; 365(Suppl 2):R37.

Significantly, it has been reported that injection of a botulinum toxin into the lower esophageal sphincter for the treatment of achalasia results in the formation of ulcers in the esophagus. Eaker, E.Y., et al., *Untoward effects of esophageal botulinum toxin injection in the treatment of achalasia*, Dig Dis Sci 1997 April; 42(4):724-7. It is know to inject a botulinum toxin into a spastic pyloric sphincter of a patient with a prepyloric ulcer in order to permit the pyloric muscle to open. Wiesel P. H. et al., *Botulinum toxin for refractory postoperative pyloric spasm*, Endoscopy 1997; 29(2):132.

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158: 1990.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscularjunction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is a biocompatible, oral formulation of a botulinum toxin.

SUMMARY

The present invention meets this need and provides a biocompatible, oral formulation of a botulinum toxin.

According to the present invention, the botulinum toxin is compounded as an oral formulation for release of the toxin active ingredient in the stomach or duodenum of a patient with a GI disorder. Preparation of an oral formulation of a botulinum toxin can be easily accomplished by mixing a lyophilized or freeze dried botulinum toxin powder with a suitable carrier such as flour, sugar or gelatin and then compressing the mixture to make an ingestible tablet. The carrier and the amount of compression is chosen so the resulting tablet (or alternately a capsule containing a therapeutic amount of the toxin mixed with or without a carrier can be formulated) is intended to be swallowed and the carrier and the characteristics of the carrier are such that the carrier rapidly dissolves in the stomach, freeing the botulinum toxin active ingredient.

The present invention provides a botulinum toxin oral formulation which overcomes the known problems, difficulties and deficiencies associated with repetitive bolus or subcutaneous injection of a botulinum toxin, to treat a GI disorder.

A botulinum toxin oral formulation within the scope of the present invention can comprise a carrier material and a botulinum toxin associated with the carrier. The toxin can be associated with the carrier by being mixed with and encapsulated by the carrier to thereby form a botulinum toxin delivery system that is a botulinum toxin oral formulation. The oral formulation can release therapeutic amounts of the botulinum toxin from the carrier in the GI tract of a patient upon oral administration.

The carrier can comprise a plurality of polymeric microspheres (i.e. a polymeric matrix) and substantial amounts of the botulinum toxin has not been transformed into a botulinum toxoid prior to association of the botulinum toxin with the carrier. That is, significant amounts of the botulinum toxin associated with the carrier have a toxicity which is substantially unchanged relative to the toxicity of the botulinum toxin prior to association of the botulinum toxin with the carrier.

According to the present invention, the botulinum toxin can be released from the carrier in the GI tract and the carrier is comprised of a substance which is substantially biodegradable. The botulinum toxin is one of the botulinum toxin types A, B, $C_1$, D, E, F and G and is preferably botulinum toxin type A. The botulinum toxin can be associated with the carrier in an amount of between about 1 unit and about 10,000 units of the botulinum toxin. Preferably, the quantity of the botulinum toxin associated with the carrier is between about 10 units and about 2,000 units of a botulinum toxin type A. Where the botulinum toxin is botulinum toxin type B, preferably, the quantity of the botulinum toxin associated with the carrier is between about 500 units and about 10,000 units of a botulinum toxin type B.

A detailed embodiment of the present invention can comprise a botulinum toxin oral formulation comprising a biodegradable polymer and between about 10 units and about 10,000 units of a botulinum toxin encapsulated by the polymer carrier, thereby forming a controlled release system, wherein therapeutic amounts of the botulinum toxin can be released from the carrier in the GI tract of a patient.

A method for making an oral formulation within the scope of the present invention can have the steps of: dissolving a polymer in a solvent to form a polymer solution; mixing or dispersing a botulinum toxin in the polymer solution to form a polymer-botulinum toxin mixture, and; allowing the polymer-botulinum toxin mixture to set or cure, thereby making an oral formulation for release of the botulinum toxin. This method can have the further step after the mixing step of evaporating solvent.

A method for using a botulinum toxin oral formulation within the scope of the present invention can be by swallowing a polymeric oral formulation which includes a botulinum toxin, thereby treating a GI disorder influenced by cholinergic innervation.

An alternate embodiment of the present invention can be a carrier comprising a polymer selected from the group of polymers consisting of polylactides and polyglycolides and a stabilized botulinum toxin associated with the carrier, thereby forming a botulinum toxin oral formulation, wherein therapeutic amounts of the botulinum toxin can be released from the carrier in the GI tract upon ingestion of the oral formulation by a human patient. The carrier can comprise a plurality of discrete sets of polymeric, botulinum toxin incorporating microspheres, wherein each set of polymers has a different polymeric composition.

The botulinum toxin used in an oral formulation according to the present invention can comprise: a first element comprising a binding element able to specifically bind to a neuronal cell surface receptor under physiological conditions, a second element comprising a translocation element able to facilitate the transfer of a polypeptide across a neuronal cell membrane, and a third element comprising a therapeutic element able, when present in the cytoplasm of a neuron, to inhibit exocytosis of acetylcholine from the neuron. The therapeutic element can cleave a SNARE protein, thereby inhibiting the exocytosis of acetylcholine from the neuron and the SNARE protein is can be selected from the group consisting of syntaxin, SNAP-25 and VAMP. Generally, the neuron affected by the botulinum toxin is a presynaptic, cholinergic neuron which innervates e.g. a GI tract muscle (smooth, striated or mixed smooth and striated muscle) or a GI tract secretory glandular tissue. Although a cholinergic neuron can show high affinity for a botulinum toxin (i.e. through a receptor for the toxin), muscle cells and gland celia can directly take up the toxin through a low affinity mechanism (i.e pinocytosis). Thus, both neurons and non-neuronal cell can be targets for the botulinum toxin.

The amount of a botulinum toxin administered by a continuous release system within the scope of the present invention during a given period can be between about $10^{-3}$ U/kg and about 35 U/kg for a botulinum toxin type A and up to about 2000 U/kg for other botulinum toxins, such as a botulinum toxin type B. 35 U/kg or 2000 U/kg is an upper limit because it approaches a lethal dose of certain neurotoxins, such as botulinum toxin type A or botulinum toxin type B, respectively. Thus, it has been reported that about 2000 units/kg of a commercially available botulinum toxin type B preparation approaches a primate lethal dose of type B botulinum toxin. Meyer K. E. et al, *A Comparative Systemic Toxicity Study of Neurobloc in Adult Juvenile Cynomolgus Monkeys*, Mov. Disord 15(Suppl 2); 54; 2000.

Preferably, the amount of a type A botulinum toxin administered by an oral formulation during a given period is between about $10^{-2}$ U/kg and about 25 U/kg. Preferably, the amount of a type B botulinum toxin administered by an oral formulation is between about $10^{-2}$ U/kg and about 1000 U/kg, since it has been reported that less than about 1000 U/kg of type B botulinum toxin can be intramuscularly administered to a primate without systemic effect. Ibid. More preferably, the type A botulinum toxin is administered in an amount of between about $10^{-1}$ U/kg and about 15 U/kg. Most preferably, the type A botulinum toxin is administered in an amount of between about 1 U/kg and about 10 U/kg. In many instances, an administration of from about 1 units to about 500 units of a botulinum toxin type A, provides effective and long lasting therapeutic relief. More preferably, from about 5 units to about 300 units of a botulinum toxin, such as a botulinum toxin type A, can be used and most preferably, from about 10 units to about 200 units of a neurotoxin, such as a botulinum toxin type A, can be locally administered to GI tract target tissue with efficacious results. In a particularly preferred embodiment of the present invention from about 1 units to about 100 units of a botulinum toxin, such as botulinum toxin type A, can be locally administered to a GI target tissue by oral administration of the disclosed oral formulation with therapeutically effective results.

The botulinum toxin can be made by *Clostridium botulinum*. Additionally, the botulinum toxin can be a modified botulinum toxin that is, a botulinum toxin that has at least one of its amino acids deleted, modified or replaced, as compared to the native or wild type botulinum toxin. Furthermore, the botulinum toxin can be a recombinant produced botulinum toxin or a derivative or fragment thereof.

Notably, it has been reported that glandular tissue treated by a botulinum toxin can show a reduced secretory activity for as long as 27 months post injection of the toxin. *Laryngoscope* 1999; 109:1344-1346, *Laryngoscope* 1998; 108:381-384.

The present invention relates to an oral formulation for the GI release of a neurotoxin and to methods for making and using such oral formulations. The oral formulation can comprise a polymer matrix containing a botulinum toxin. The oral formulation is designed to administer effective levels of neurotoxin when orally administered.

This invention further relates to a composition, and methods of making and using the composition, for the controlled of biologically active, stabilized neurotoxin. The controlled release composition of this invention can comprise a polymeric matrix of a biocompatible polymer and biologically active, stabilized neurotoxin dispersed within the biocompatible polymer.

DEFINITIONS

The following definitions apply herein.

"About" means plus or minus ten percent of the value so qualified.

"Biocompatible" means that there is an insignificant inflammatory response upon ingestion of the oral formulation.

"Biologically active compound" means a compound which can effect a beneficial change in the subject to which it is administered. For example, "biologically active compounds" include neurotoxins.

"Effective amount" as applied to the biologically active compound means that amount of the compound which is generally sufficient to effect a desired change in the subject. For example, where the desired effect is a flaccid muscle paralysis, an effective amount of the compound is that amount which causes at least a substantial paralysis of the desired muscles without causing a substantial paralysis of adjacent muscle of which paralysis is not desired, and without resulting in a significant systemic toxicity reaction.

"Effective amount" as applied to a non-active ingredient constituent of an oral formulation (such as a polymer used for forming a matrix or a coating composition) refers to that amount of the non-active ingredient constituent which is sufficient to positively influence the release of a biologically active agent at a desired rate for a desired period of time. For example, where the desired effect is muscle paralysis by using a single oral formulation, the "effective amount" is the amount that can facilitate extending the release over a period of between about 60 days and 6 years. This "effective amount" can be determined based on the teaching in this specification and the general knowledge in the art.

"Effective amount" as applied to the amount of surface area of an oral formulation is that amount of oral formulation surface area which is sufficient to effect a flux of biologically active compound so as to achieve a desired effect, such as a muscle paralysis or a decrease in the secretory activity of a gland. The area necessary may be determined and adjusted directly by measuring the release obtained for the particular active compound. The surface area of the oral formulation or of a coating of an oral formulation is that amount of membrane necessary to completely encapsulate the biologically active compound. The surface area depends on the geometry of the oral formulation. Preferably, the surface area is minimized where possible, to reduce the size of the oral formulation.

"Oral formulation" means a drug delivery system. The oral formulation is comprised of a biocompatible polymer or natural material which contains or which can act as a carrier for a molecule with a biological activity. The oral formulation is intended for swallowing by a human patient.

"Neurotoxin" means an agent which can interrupt nerve impulse transmission across a neuromuscular or neuroglandular junction, block or reduce neuronal exocytosis of a neurotransmitter or alter the action potential at a sodium channel voltage gate of a neuron. Examples of neurotoxins include botulinum toxins, tetanus toxins, saxitoxins, and tetrodotoxin.

"Treatment" means any treatment of a disease in a mammal, and includes: (i) preventing the disease from occurring or; (ii) inhibiting the disease, i.e., arresting its development; (iii) relieving the disease, i.e., reducing the incidence of symptoms of or causing regression of the disease.

A method for making an oral formulation within the scope of the present invention for controlled release of a neurotoxin, can include dissolving a biocompatible polymer in a polymer solvent to form a polymer solution, dispersing particles of biologically active, stabilized neurotoxin in the polymer solution, and then solidifying the polymer to form a polymeric matrix containing a dispersion of the neurotoxin particles.

The present invention encompasses a solid form botulinum toxin oral formulation which comprises a botulinum toxin and a carrier associated with the botulinum toxin to thereby forming a solid form botulinum toxin oral formulation. The carrier can be formulated to dissolve in and thereby release in the gastrointestinal tract of a patient therapeutic amounts of the botulinum toxin in a gastrointestinal tract of a patient. Additionally, the solid form botulinum toxin formulation can exhibit a gastric retention due to a method selected from the group consisting of mucoadhesion, flotation, sedimentation, expansion, or simultaneous administration of pharmacological agent to delay gastric emptying. By "gastric retention" it is meant that the oral formulation has a residency time which is greater that the GI tract residency time of a typically ingested food stuff or nutrient which is not treated so as to show a characteristic of mucoadhesion, flotation, sedimentation, expansion, or which is not simultaneously administered with a pharmacological agent which acts to delay gastric emptying.

Preferably, the oral formulation does not comprise substantial amounts of the botulinum toxin which has been transformed into a botulinum toxoid prior to association of the botulinum toxin with the carrier. Thus, the oral formulation preferably comprises botulinum toxin associated with the carrier which toxin has a toxicity which is substantially unchanged relative to the toxicity of the botulinum toxin prior to association of the botulinum toxin with the carrier.

The carrier of the oral formulation can comprise a biocompatible, biodegradable substance selected from the group consisting of flour, sugar and gelatin. The botulinum toxin of the oral formulation of can be selected from the group consisting of botulinum toxin types A, B, $C_1$, D, E, F and G. Preferably, the botulinum toxin is a botulinum toxin type A. The quantity of the botulinum toxin associated with the carrier is between about 1 unit and about 10,000 units of the botulinum toxin or between about 10 units and about 2,000 units of a botulinum toxin type A.

The botulinum toxin can comprise a first element comprising a binding element able to specifically bind to a neuronal cell surface receptor under physiological conditions; a second element comprising a translocation element able to facilitate the transfer of a polypeptide across a neuronal cell membrane, and a third element comprising a therapeutic element able, when present in the cytoplasm of a neuron, to inhibit exocytosis of acetylcholine from the neuron. The therapeutic element can cleave a SNARE protein, thereby inhibiting the exocytosis of acetylcholine from the neuron. The SNARE protein can be selected from the group consisting of syntaxin, SNAP-25 and VAMP.

An alternate botulinum toxin oral formulation within the scope of the present invention can comprise a botulinum toxin type A and a carrier associated with the botulinum toxin type A, thereby forming a botulinum toxin oral formulation, wherein the carrier is formulated to release therapeutic amounts of the botulinum toxin type A in a gastrointestinal tract of a patient with a gastric ulcer without a significant immune system response, and wherein the carrier comprises a biocompatible, biodegradable substance, and wherein a controlled gastric retention the solid form can be achieved by a method selected from the group consisting of mucoadhesion, flotation, sedimentation, expansion, or by a simultaneous administration of pharmacological agents which delay gastric emptying.

An further formulation within the scope of the present invention can comprise a botulinum toxin formulation for oral administration to a patient with a gastrointestinal tract comprising biologically active botulinum toxin, and a biocompatible, biodegradable and non-toxic carrier associated with the botulinum toxin, wherein the carrier has a characteristic of rapidly degrading in a gastrointestinal system of a patient to thereby release a therapeutic amount the biologically active botulinum toxin into the gastrointestinal system of the patient, without a significant immune system response to the ingested botulinum toxin.

The oral formulation's carrier can comprise a plurality of polymeric microspheres or the carrier can comprise a polymeric matrix. A method within the scope of the present invention can comprise a method for using a botulinum toxin oral formulation the method comprising the step of ingesting an oral formulation of a botulinum toxin.

A detailed embodiment within the scope of the present invention can be a botulinum toxin oral formulation comprising:
  (a) a carrier comprising a polymer selected from the group of polymers consisting of polylactides, polyglycolides and polyanhydrides;
  (b) a stabilized botulinum toxin associated with the carrier, thereby forming a botulinum oral formulation,
wherein therapeutic amounts of the botulinum toxin can be released from the carrier in a GI tract of a patient.

DESCRIPTION

The present invention is based upon the discovery of a therapeutically effective oral formulation of a botulinum toxin. Thus, I have discovered that ingestion of a botulinum toxin, such as a botulinum toxin type A, mixed with a suitable carrier, which dissolves in the gastrointestinal tract, permits delivery of therapeutic amounts of a bioactive botulinum toxin to and to the vicinity of a gastrointestinal disorder. Typically, within a few days thereafter the GI disorder shows unmistakable signs of healing (remission) and can be completely cured within a few weeks after administration of the oral botulinum toxin formulation. Side effects can include a reduced motility of gastrointestinal muscles and weight loss.

The therapeutic dose of orally administered botulinum toxin is such that there are nominal or insignificant systemic effects due to any botulinum toxin which is absorbed through the gut lining into the circulatory system. Thus, 200 units of botulinum toxin can be injected into the pyloric (lower stomach) sphincter of patients with diabetic gastroparesis without any ensuing systemic toxicity. Crowell, M. D., et al., *Botulinum toxin reduces pyloric dysfunction in patients with diabetic gastroparesis*, Gastroenterology 2002 April; 122(4 Supp 1):A451-A452. Although there is no evidence for a teratogenic effect by a botulinum toxin, methods within the scope of my invention disclosed herein are not intended for application to or by a patient who is pregnant, nursing or who intends to become pregnant during the treatment period.

Without wishing to be bound by theory, a physiological mechanism can be proposed for the efficacy of the present invention. Thus, it is well known that botulinum toxin acts on cholinergic nerves, including those in the gastrointestinal tract responsible for the motility of GI muscles. Pasricha, P. J., *Botulinum toxin for spastic gastrointestinal disorders*, Bailliere's Clin Gastroenterol 1999; 13(1):131-143. Additionally, gastrin secretion and HCL production by gastric parietal cells is strongly dependant upon cholinergic activity of vagal and myenteric fibers which act on neuroglandular junctions in the gastrointestinal tract. Rossi S., et al., *Immunohistochemical localization of SNAP-25 protein in the stomach of rat*, Naunyn Schmiedebergs Arch Pharmacol 2002; 365(Suppl 2):R37. Furthermore, the intracellular substrate (SNAP-25) for botulinum toxin type A BTX-A is present in stomach wall cells. Gui D., et al., *Effects of botulinum toxin on gastric emptying and digestive secretions. A possible tool for correction of obesity?*, Naunyn Schmiedebergs Arch Pharmacol 2002 June; 365(Suppl 2):R22. Thus, an oral formulation of a botulinum toxin can be used to treat many different GI disorders by e.g. reducing the motility of a cholinergically innervated gastrointestinal muscle or by reducing an excessive secretion from a cholinergically innervated gastrointestinal gland.

An orally administered botulinum toxin can remain bioactive in the harsh environment of the GI tract. Thus, botulinum toxin is secreted by a Clostridial bacterium as a complex which comprises the approximately 150 kDa single chain protein toxin molecule surrounded by a number of non-toxin protein molecules. Significantly, the non toxin proteins act to protect the toxin from acid hydrolysis and enzymatic degradation during passage of the complex through the GI tract, so that the toxin complex is able to survive the harsh conditions of extremes of pH and proteolytic enzymes and yet still function as a highly potent neurotoxin. It has been demonstrated that the non-toxin proteins which are complexed with the botulinum toxin molecule act to protect the 150 kDa toxin molecule in the gastrointestinal tract from digestive acids. Hanson, M. A. et al., *Structural view of botulinum neurotoxin in numerous functional states*, being chapter 2, pages 11-27 of Brin M. F. et al, editors, *Scientific and therapeutic aspects of botulinum Toxin*, Lippincott, Williams & Wilkins (2002).

A botulinum toxin oral formulation within the scope of the present invention is capable of releasing a therapeutic amount of a botulinum toxin into the GI tract of a patient with a GI disorder. The amount of released botulinum toxin can comprise (for a botulinum toxin type A) as little as about 10 units (i.e. to treat a GI motility disorder in an infant) to as much as 500 units (i.e. to treat multiple excessively secreting GI glands in a large adult). The quantity of botulinum toxin required for therapeutic efficacy can be varied according to the known clinical potency of the different botulinum toxin serotypes. For example, several orders of magnitude more units of a botulinum toxin type B are typically required to achieve a physiological effect comparable to that achieved from use of a botulinum toxin type A.

The botulinum toxin released in therapeutically effective amounts by an oral formulation within the scope of the present invention is preferably, substantially biologically active botulinum toxin. In other words, the botulinum toxin released from the oral formulation is capable of binding with high affinity to a cholinergic neuron, being translocated, at least in part, across the neuronal membrane, and through its activity in the cytosol of the neuron of inhibiting exocytosis of acetylcholine from the neuron. The present invention excludes from its scope use deliberate use of a botulinum toxoid as an antigen in order to confer immunity to the botulinum toxin through development of antibodies (immune response) due to the immunogenicity of the toxoid. The purpose of the present invention is to permit a release of minute amounts of a botulinum toxin from an orally administered formulation as to inhibit exocytosis in vivo in a patent's GI tract and thereby achieve a desired therapeutic effect, such as reduction of muscle spasm or muscle tone, preventing a muscle from contracting or to reduce an excessive secretion from a cholinergically influenced secretory cell or gland in the gastrointestinal tract.

The oral formulation is prepared so that the botulinum toxin is substantially uniformly dispersed in a biodegradable carrier. An alternate oral formulation within the scope of the present invention can comprise a carrier coated by a biodegradable coating, either the thickness of the coating or the coating material being varied.

The thickness of the oral formulation can be used to control the absorption of water by, and thus the rate of release of a neurotoxin from, a composition of the invention, thicker oral formulations releasing the polypeptide more slowly than thinner ones.

The neurotoxin in a neurotoxin controlled release composition can also be mixed with other excipients, such as bulking agents or additional stabilizing agents, such as buffers to stabilize the neurotoxin during lyophilization.

The carrier is preferably comprised of a non-toxic, non-immunological, biocompatible material. Suitable oral formulation materials can include polymers of poly(2-hydroxy ethyl methacrylate) (p-HEMA), poly(N-vinyl pyrrolidone) (p-NVP)⁺, poly(vinyl alcohol) (PVA), poly(acrylic acid) (PAA), polydimethyl siloxanes (PDMS), ethylene-vinyl acetate copolymers (EVAc), a polymethylmethacrylate (PMMA), polyvinylpyrrolidone/methylacrylate copolymers, poly(lactic acid) (PLA), poly(glycolic acid) (PGA), polyanhydrides, poly(ortho esters), collagen and cellulosic derivatives and bioceramics, such as hydroxyapatite (HPA), tricalcium phosphate (TCP), and aliminocalcium phosphate (ALCAP).

Biodegradable carriers can be made from polymers of poly (lactides), poly(glycolides), collagens, poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polycyanoacrylates, poly(p-dioxanone), poly (alkylene oxalates), biodegradable polyurethanes, blends and copolymers thereof. Particularly preferred carriers are formed as polymers or copolymers of poly(lactic-co-glycolic acid) ("PLGA"), where the lactide:glycolide ratio can be varied depending on the desired carrier degradation rate.

Biodegradable PLGA polymers have been used to form resorbable sutures and bone plates and in several commercial microparticle formulations. PLGA degrades through bulk erosion to produce lactic and glycolic acid and is commercially available in a variety of molecular weight and polymer end groups (e.g. lauryl alcohol or free acid). Polyanhydrides are another group of polymers that have been approved for use in humans, and have been used to deliver proteins and antigens. Unlike PLGA, polyanhydrides degrade by surface erosion, releasing neurotoxin entrapped at the carrier surface.

To prepare a suitable oral formulation, the carrier polymer can be dissolved in an organic solvent such as methylene chloride or ethyl acetate and the botulinum toxin can then be mixed into the polymer solution. The conventional processes for microsphere formation are solvent evaporation and solvent (coacervation) methods. The water-in-oil-in-water (W/O/W) double emulsion method is a widely used method of protein antigen encapsulation into PLGA microspheres.

An aqueous solution of a botulinum toxin also can be used to make an oral formulation. An aqueous solution of the neurotoxin is added to the polymer solution (polymer previously dissolved in a suitable organic solvent). The volume of the aqueous (neurotoxin) solution relative to the volume of organic (polymer) solvent is an important parameter in the determination of both the release characteristics of the microspheres and with regard to the encapsulation efficiency (ratio of theoretical to experimental protein loading) of the neurotoxin.

The encapsulation efficiency can also be increased by increasing the kinematic viscosity of the polymer solution. The kinematic viscosity of the polymer solution can be increased by decreasing the operating temperature and/or by increasing the polymer concentration in the organic solvent.

Thus, with a low aqueous phase (neurotoxin) to organic phase (polymer) volume ratio (i.e. aqueous volume:organic volume is ≤0.1 ml/ml) essentially 100% of the neurotoxin can be encapsulated by the microspheres and the microspheres can show a triphasic release: an initial burst (first pulse), a lag phase with little or no neurotoxin being released and a second release phase (second pulse).

The length of the lag phase is dependent upon the polymer degradation rate which is in turn dependant upon polymer composition and molecular weight. Thus, the lag phase between the first (burst) pulse and the second pulse increases as the lactide content is increased, or as the polymer molecular weight is increased with the lactide:glycolide ratio being held constant. In addition to a low aqueous phase (neurotoxin) volume, operation at low temperature (2-8 degrees C.), as set forth above, increases the encapsulation efficiency, as well as reducing the initial burst and promoting increased neurotoxin stability against thermal inactivation Suitable oral formulations within the scope of the present invention for the controlled in vivo release of a neurotoxin, such as a botulinum toxin, can be prepared so that the oral formulation releases the neurotoxin in the GI tract.

Preferably, an oral formulation releases the botulinum toxin with negligible serum levels of the toxin. An oral formulation within the scope of the present invention can also be formulated as a suspension for ingestion. Such suspensions may be manufactured by general techniques well known in the pharmaceutical art, for example by milling the polylactide/polypeptide mixture in an ultracentrifuge mill fitted with a suitable mesh screen, for example a 120 mesh, and suspending the milled, screened particles in a solvent for injection, for example propylene glycol, water optionally with a conventional viscosity increasing or suspending agent, oils or other known, suitable liquid vehicles for oral ingestion.

Preferably, the release of biologically active neurotoxin in vivo does not result in a significant immune system response during the release period of the neurotoxin.

A botulinum toxin oral formulation preferably permits botulinum release from biodegradable polymer microspheres in a biologically active form that is, with a substantially native toxin conformation. To stabilize a neurotoxin, both in a format which renders the neurotoxin useful for mixing with a suitable polymer which can form the oral formulation matrix (i.e. a powdered neurotoxin which has been freeze dried or lyophilized) as well as while the neurotoxin is present or incorporated into the matrix of the selected polymer, various pharmaceutical excipients can be used. Suitable excipients can include starch, cellulose, talc, glucose, lactose, sucrose, gelatin, malt, rice, flour, chalk, silica gel, magnesium stearate, sodium stearate, glycerol monostearate, sodium chloride, albumin and dried skim milk. The neurotoxin in a neurotoxin oral formulation can be mixed with excipients, bulking agents and stabilizing agents, and buffers to stabilize the neurotoxin during lyophilization or freeze drying.

It has been discovered that a stabilized neurotoxin can comprise biologically active, non-aggregated neurotoxin complexed with at least one type of multivalent metal cation which has a valiancy of +2 or more.

Suitable multivalent metal cations include metal cations contained in biocompatible metal cation components. A metal cation component is biocompatible if the cation component is non-toxic to the recipient, in the quantities used, and also presents no significant deleterious or untoward effects on the recipient's body, such as an immunological reaction upon oral administration of the formulation.

Preferably, the molar ratio of metal cation component to neurotoxin, for the metal cation stabilizing the neurotoxin, is between about 4:1 to about 100:1 and more typically about 4:1 to about 10:1.

A preferred metal cation used to stabilize a botulinum toxin is $Zn^{++}$ because the botulinum toxin are known to be zinc endopeptidases. Divalent zinc cations are preferred because botulinum toxin is known to be a divalent zinc endopeptidase. In a more preferred embodiment, the molar ratio of metal cation component, containing $Zn^{++}$ cations, to neurotoxin is about 6:1.

The suitability of a metal cation for stabilizing neurotoxin can be determined by one of ordinary skill in the art by performing a variety of stability indicating techniques such as polyacrylamide gel electrophoresis, isoelectric focusing, reverse phase chromatography, HPLC and potency tests on neurotoxin lyophilized particles containing metal cations to determine the potency of the neurotoxin after lyophilization and for the duration of release from microparticles. In stabilized neurotoxin, the tendency of neurotoxin to aggregate within a microparticle during hydration in vivo and/or to lose biological activity or potency due to hydration or due to the process of forming a sustained release composition, or due to the chemical characteristics of a sustained release composition, is reduced by complexing at least one type of metal cation with neurotoxin prior to contacting the neurotoxin with a polymer solution.

By the present invention, stabilized neurotoxin is stabilized against significant aggregation in vivo over the controlled release period. Significant aggregation is defined as an amount of aggregation resulting in aggregation of about 15% or more of the polymer encapsulated or polymer matrix incorporated neurotoxin. Preferably, aggregation is maintained below about 5% of the neurotoxin. More preferably, aggregation is maintained below about 2% of the neurotoxin present in the polymer.

In another embodiment, a neurotoxin controlled release composition also contains a second metal cation component, which is not contained in the stabilized neurotoxin particles, and which is dispersed within the carrier. The second metal cation component preferably contains the same species of metal cation, as is contained in the stabilized neurotoxin. Alternately, the second metal cation component can contain one or more different species of metal cation.

The second metal cation component acts to modulate the release of the neurotoxin from the polymeric matrix of the oral formulation, such as by acting as a reservoir of metal cations to further lengthen the period of time over which the neurotoxin is stabilized by a metal cation to enhance the stability of neurotoxin in the composition.

A metal cation component used in modulating release typically contains at least one type of multivalent metal cation. Examples of second metal cation components suitable to modulate neurotoxin release, include, or contain, for instance, $Mg(OH)_2$, $MgCO_3$ (such as $4MgCO_3Mg(OH)_2 5H_2O$), $ZnCO_3$ (such as $3Zn(OH)_2 2ZnCO_3$), $CaCO_3$, $Zn_3 (C_6H_5O_7)_2$, $Mg(OAc)_2$, $MgSO_4$, $Zn(OAc)_2$, $ZnSO_4$, $ZnCl_2$, $MgCl_2$ and $Mg_3 (C_6H_5O_7)_2$. A suitable ratio of second metal cation component-to-polymer is between about 1:99 to about 1:2 by weight. The optimum ratio depends upon the polymer and the second metal cation component utilized.

The neurotoxin oral formulation of this invention can be formed into many shapes such as a film, a pellet, a cylinder, a disc or a microsphere. A microsphere, as defined herein, comprises a carrier component having a diameter of less than about one millimeter and having stabilized neurotoxin dispersed therein. A microsphere can have a spherical, non-spherical or irregular shape. It is preferred that a microsphere be spherical in shape. Typically, the microsphere will be of suspended in a suitable liquid for ingestion. A preferred size range for microspheres is from about 1 to about 180 microns in diameter.

In the method of this invention for forming a composition for GI release of biologically active, non-aggregated neurotoxin, a suitable amount of particles of biologically active, stabilized neurotoxin are dispersed in a carrier.

A suitable polymer carrier solvent, as defined herein, is solvent in which the polymer is soluble but in which the stabilized neurotoxin is are substantially insoluble and non-reactive. Examples of suitable polymer solvents include polar organic liquids, such as methylene chloride, chloroform, ethyl acetate and acetone.

To prepare biologically active, stabilized neurotoxin, neurotoxin is mixed in a suitable aqueous solvent with at least one suitable metal cation component under pH conditions suitable for forming a complex of metal cation and neurotoxin. Typically, the complexed neurotoxin will be in the form of a cloudy precipitate, which is suspended in the solvent. However, the complexed neurotoxin can also be in solution. In an even more preferred embodiment, neurotoxin is complexed with $Zn^{++}$.

Suitable pH conditions to form a complex of neurotoxin typically include pH values between about 5.0 and about 6.9. Suitable pH conditions are typically achieved through use of an aqueous buffer, such as sodium bicarbonate, as the solvent.

Suitable solvents are those in which the neurotoxin and the metal cation component are each at least slightly soluble, such as in an aqueous sodium bicarbonate buffer. For aqueous solvents, it is preferred that water used be either deionized water or water-for-injection (WFI).

The neurotoxin can be in a solid or a dissolved state, prior to being contacted with the metal cation component. Additionally, the metal cation component can be in a solid or a dissolved state, prior to being contacted with the neurotoxin. In a preferred embodiment, a buffered aqueous solution of neurotoxin is mixed with an aqueous solution of the metal cation component.

Typically, the complexed neurotoxin will be in the form of a cloudy precipitate, which is suspended in the solvent. However, the complexed neurotoxin can also be in solution. In a preferred embodiment, the neurotoxin is complexed with $Zn^{++}$.

The $Zn^{++}$ complexed neurotoxin can then be dried, such as by lyophilization, to form particulates of stabilized neurotoxin. The $Zn^{++}$ complexed neurotoxin, which is suspended or in solution, can be bulk lyophilized or can be divided into smaller volumes which are then lyophilized. In a preferred embodiment, the $Zn^{++}$ complexed neurotoxin suspension is micronized, such as by use of an ultrasonic nozzle, and then lyophilized to form stabilized neurotoxin particles. Acceptable means to lyophilize the $Zn^{++}$ complexed neurotoxin mixture include those known in the art.

In another embodiment, a second metal cation component, which is not contained in the stabilized neurotoxin particles, is also dispersed within the polymer solution.

It is understood that a second metal cation component and stabilized neurotoxin can be dispersed into a polymer solution sequentially, in reverse order, intermittently, separately or through concurrent additions. Alternately, a polymer, a second metal cation component and stabilized neurotoxin and can be mixed into a polymer solvent sequentially, in reverse order, intermittently, separately or through concurrent additions. In this method, the polymer solvent is then solidified to form a polymeric matrix containing a dispersion of stabilized neurotoxins.

A suitable method for forming an neurotoxin oral formulations from a polymer solution is the solvent evaporation method is described in U.S. Pat. Nos. 3,737,337; 3,523,906; 3,691,090; and 4,389,330. Solvent evaporation can be used as a method to form a neurotoxin oral formulation.

In the solvent evaporation method, a polymer solution containing a stabilized neurotoxin particle dispersion, is mixed in or agitated with a continuous phase, in which the polymer solvent is partially miscible, to form an emulsion. The continuous phase is usually an aqueous solvent. Emulsifiers are often included in the continuous phase to stabilize the emulsion. The polymer solvent is then evaporated over a period of several hours or more, thereby solidifying the polymer to form a polymeric matrix having a dispersion of stabilized neurotoxin particles contained therein.

A preferred method for forming neurotoxin controlled release microspheres from a polymer solution is described in U.S. Pat. No. 5,019,400. This method of microsphere formation, as compared to other methods, such as phase separation, additionally reduces the amount of neurotoxin required to produce an oral formulation with a specific neurotoxin content.

In this method, the polymer solution, containing the stabilized neurotoxin dispersion, is processed to create droplets, wherein at least a significant portion of the droplets contain polymer solution and the stabilized neurotoxin. These droplets are then frozen by means suitable to form microspheres. Examples of means for processing the polymer solution dispersion to form droplets include directing the dispersion through an ultrasonic nozzle, pressure nozzle, Rayleigh jet, or by other known means for creating droplets from a solution.

The solvent in the frozen microdroplets is extracted as a solid and/or liquid into the non-solvent to form stabilized neurotoxin containing microspheres. Mixing ethanol with other non-solvents, such as hexane or pentane, can increase the rate of solvent extraction, above that achieved by ethanol alone, from certain polymers, such as poly(lactide-co-glycolide) polymers.

Yet another method of forming a neurotoxin oral formulation, from a polymer solution, includes film casting, such as in a mold, to form a film or a shape. For instance, after putting the polymer solution containing a dispersion of stabilized neurotoxin into a mold, the polymer solvent is then removed by means known in the art, or the temperature of the polymer solution is reduced, until a film or shape, with a consistent dry weight, is obtained.

In the case of a biodegradable polymer oral formulation, release of neurotoxin occurs due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer. Hydrophilic excipients such as salts, carbohydrates and surfactants can also be incorporated to increase hydration and which can alter the rate of erosion of the polymer.

By altering the properties of a biodegradable polymer, the contributions of diffusion and/or polymer degradation to neurotoxin release can be controlled. For example, increasing the glycolide content of a poly(lactide-co-glycolide) polymer and decreasing the molecular weight of the polymer can enhance the hydrolysis of the polymer and thus, provides an increased neurotoxin release from polymer erosion. In addition, the rate of polymer hydrolysis is increased in non-neutral pHs. Therefore, an acidic or a basic excipient can be added to the polymer solution, used to form the microsphere, to alter the polymer erosion rate.

An oral formulation within the scope of the present invention can be administered to a human to provide the desired dosage of neurotoxin based on the known parameters for treatment with neurotoxin of various medical conditions, as previously set forth.

The specific dosage by oral formulation appropriate for administration is readily determined by one of ordinary skill in the art according to the factors discussed above. The dosage can also depend upon the size of the tissue mass to be treated or denervated, and the commercial preparation of the toxin. Additionally, the estimates for appropriate dosages in humans can be extrapolated from determinations of the amounts of botulinum required for effective denervation of other tissues. Thus, the amount of botulinum A to be injected is proportional to the mass and level of activity of the tissue to be treated. Generally, between about 0.01 units per kilogram to about 35 units per kg of patient weight of a botulinum toxin, such as botulinum toxin type A, can be released by the present oral formulation per unit time period (i.e. over a period of or once every 2-4 months) to effectively accomplish a desired muscle paralysis. Less than about 0.01 U/kg of a botulinum toxin does not have a significant therapeutic effect upon a muscle, while more than about 35 U/kg of a botulinum toxin approaches a toxic dose of a neurotoxin, such as a botulinum toxin type A. Careful preparation of the oral formulation prevents significant amounts of a botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the tissue to be treated and the administration route chosen. Botulinum toxin type A is a preferred botulinum toxin serotype for use in the methods of the present invention.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known safe and efficacious use for the treatment of skeletal muscle and smooth muscle disorders when locally administered by intramuscular injection.

The present invention includes within its scope the use of any neurotoxin which has a long duration therapeutic effect when used to treat a movement disorder or an affliction influenced by cholinergic innervation. For example, neurotoxins made by any of the species of the toxin producing *Clostridium* bacteria, such as *Clostridium botulinum, Clostridium butyricum*, and *Clostridium beratti* can be used or adapted for use in the methods of the present invention. Additionally, all of the botulinum serotypes A, B, C, D, E, F and G can be advantageously used in the practice of the present invention, although type A is the most preferred serotype, as explained above. Practice of the present invention can provide effective relief for from 1 month to about 5 or 6 years.

The present invention includes within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for a cell surface receptor present on a cell.

Botulinum toxins for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

The present invention also includes within its scope the use of an oral formulation so as to provide therapeutic relief from a GI disorder. Thus, the neurotoxin can be imbedded within, absorbed, or carried by a suitable polymer matrix which can be swallowed.

Methods for determining the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., 14$^{th}$ edition, published by McGraw Hill). Thus, an oral formulation within the scope of the present invention can be administered by being swallowed.

It is known that a significant water content of lyophilized tetanus toxoid can cause solid phase aggregation and inactivation of the toxoid once encapsulated within microspheres. Thus, with a 10% (grams of water per 100 grams of protein) tetanus toxoid water content about 25% of the toxin undergoes aggregation, while with a 5% water content only about 5% of the toxoid aggregates. See e.g. Pages 251, Schwendeman S. P. et al., *Peptide, Protein, and Vaccine Delivery From Oral formulationable Polymeric Systems*, chapter 12 (pages 229-267) of Park K., *Controlled Drug Delivery Challenges and Strategies*, American Chemical Society (1997). Significantly, the manufacturing process for BOTOX® results in a freeze dried botulinum toxin type A complex which has a moisture content of less than about 3%, at which moisture level nominal solid phase aggregation can be expected.

A general procedure for making a, biodegradable botulinum toxin oral formulation is as follows. The oral formulation can comprise from about 25% to about 100% of a polylactide which is a polymer of lactic acid alone. Increasing the amount of lactide in the oral formulation can increases the period of time before which the oral formulation begins to biodegrade, and hence increases the time to release of the botulinum toxin from the oral formulation. The oral formulation can also be a copolymer of lactic acid and glycolic acid. The lactic acid can be either in racemic or in optically active form, and can be either soluble in benzene and having an inherent viscosity of from 0.093 (1 g. per 100 ml. in chloroform) to 0.5 (1 g. per 100 ml. in benzene), or insoluble in benzene and having an inherent viscosity of from 0.093 (1 g. per 100 ml in chloroform) to 4 (1 g. per 100 ml in chloroform or dioxin). The oral formulation can also comprise from 0.001% to 50% of a botulinum toxin uniformly dispersed in carrier polymer.

Once an oral formulation begins to absorb water it can exhibit two successive and generally distinct phases of neurotoxin release. In the first phase neurotoxin is released through by initial diffusion through aqueous neurotoxin regions which communicate with the exterior surface of the oral formulation. The second phase occurs upon release of neurotoxin consequent to degradation of the biodegradable carrier (i.e. a polylactide). The diffusion phase and the degradation-induced phase can be temporally distinct in time. When the oral formulation is placed in an aqueous physiological environment, water diffuses into the polymeric matrix and is partitioned between neurotoxin and polylactide to form aqueous neurotoxin regions. The aqueous neurotoxin regions increase with increasing absorption of water, until the continuity of the aqueous neurotoxin regions reaches a sufficient level to communicate with the exterior surface of the oral formulation. Thus, neurotoxin starts to be released from the oral formulation by diffusion through aqueous polypeptide channels formed from the aqueous neurotoxin regions, while the second phase continues until substantially all of the remaining neurotoxin has been released.

Also within the scope of the present invention is an oral formulation in the form of a suspension prepared by suspending the neurotoxin encapsulated microspheres in a suitable liquid, such as physiological saline.

EXAMPLES

The following examples set forth specific compositions and methods encompassed by the present invention and are not intended to limit the scope of the present invention.

Example 1

Method For Making a Botulinum Toxin Tablet for Oral Ingestion

A botulinum toxin can be compounded as an oral formulation for release of the toxin active ingredient into the stomach or duodenum. This is easily accomplished by mixing with a mortar and pestle (at room temperature without addition of any water or saline) 50 units of a commercially available lyophilized botulinum toxin powder, such as non-reconstituted BOTOX® (or 200 units of DYSPORT® powder) with a biodegradable carrier such as flour or sugar. Alternately, the botulinum toxin can be mixed by homogenization or sonication to form a fine dispersion of the powdered toxin in the carrier. The mixture can then compressed with a tablet making machine (such as the tablet press available from Scheu & Kniss, 1500 W. Ormsby Ave, Louisville, Ky. 40210) to make an ingestible tablet. Alternately, the toxin can be formulated with gelatin by well known methodologies to make an ingestible geltab.

Example 2

Method For Treating Obesity

An obese 42 year old male is treated by administration of the botulinum toxin oral formulation of Example 1. The patient swallows one 50 units type A tablet during each of four days. Within two weeks the patient has lost ten pounds, and the weight loss increases to 20 pounds by the end of the fourth week, due apparently to reduced gastrointestinal motility.

Example 3

Method for Making a Biodegradable Botulinum Toxin Oral Formulation

A biodegradable oral formulation comprising botulinum toxin and a suitable carrier polymer can be prepared by dispersing an appropriate amount of a stabilized botulinum toxin preparation (i.e. non-reconstituted BOTOX®) into a continuous phase consisting of a biodegradable polymer in a volatile organic solvent, such as dichloromethane. Both PLGA and polyanhydrides are insoluble in water and require use of organic solvents in the microencapsulation process.

The polymer is dissolved in an organic solvent such as methylene chloride or ethyl acetate to facilitate microsphere fabrication. The botulinum toxin is then mixed by homogenization or sonication to form a fine dispersion of toxin in polymer/organic solvent, as an emulsion when an aqueous protein solution is used or as a suspension when a solid protein formulation is mixed with the polymer-organic solvent solution. The conventional processes for microsphere formation are solvent evaporation and solvent (coacervation) methods. Microspheres can be formed by mixing the preformed suspension of protein drug with polymer-organic solvent, with water containing an emulsifier (i.e. polyvinyl alcohol). Additional water is then added to facilitate removal of the organic solvent from the microspheres allowing them to harden. The final microspheres are dried to produce a free flowing powder.

The polymer used can be PLA, PGA or a co-polymer thereof. Alternately, a botulinum toxin incorporating polymer can be prepared by emulsifying an aqueous solution of the neurotoxin (i.e. reconstituted BOTOX®) into the polymer-organic phase (obtaining thereby a W/O emulsion). With either process a high speed stirrer or ultrasound is used to ensure uniform toxin mixing with the polymer. Microparticles 1-50 μm in diameter can be formed by atomizing the emulsion into a stream of hot air, inducing the particle formation through evaporation of the solvent (spray-drying technique). Alternately, particle formation can be achieved by coacervation of the polymer through non-solvent addition, e.g. silicon oil (phase separation technique) or by preparing a W/O/W emulsion (double emulsion technique).

The pH of the casting or other solution in which the botulinum toxin is to be mixed is maintained at pH 4.2-6.8, because at pH above about pH 7 the stabilizing nontoxin proteins can dissociate from the botulinum toxin resulting in gradual loss of toxicity. Preferably, the pH is between about 5-6. Furthermore the temperature of the mixture/solution should not exceed about 35 degrees Celsius, because the toxin can be readily detoxified when in a solution/mixture heated above about 40 degrees Celsius.

Methods for freezing droplets to form microparticles include directing the droplets into or near a liquefied gas, such as liquid argon and liquid nitrogen to form frozen microdroplets which are then separated from the liquid gas. The frozen microdroplets can then be exposed to a liquid non-solvent, such as ethanol, or ethanol mixed with hexane or pentane.

A wide range of sizes of botulinum toxin oral formulation microparticles can be made by varying the droplet size, for example, by changing the ultrasonic nozzle diameter. If very large microparticles are desired, the microparticles can be extruded through a syringe directly into the cold liquid. Increasing the viscosity of the polymer solution can also increase microparticle size. The size of the microparticles can be produced by this process, for example microparticles ranging from greater than about 1000 to about 1 micrometers in diameter. An ingestible capsule can then be filled with the botulinum toxin incorporating microparticles and sealed to make a botulinum toxin oral formulation.

Alternately, the capsule can just be filled with an appropriate amount of non-reconstituted BOTOX (not further processed into microspheres) powder admixed with a suitable amount of an inert carrier such as flour or sugar, so as to provide enough volume of material to fill the capsule.

Example 4

Method for Making a Polyanhydride Botulinum Toxin Oral Formulation

A biodegradable polyanhydride polymer can be made as a copolymer of poly-carboxyphenoxypropane and sebacic acid in a ratio of 20:80. Polymer and a botulinum toxin (such as non-reconstituted BOTOX®) can be co-dissolved in methylene chloride at room temperature and spray-dried into microspheres, using the technique of Example 3. Any remaining methylene chloride can be evaporated in a vacuum desiccator.

Depending upon the oral formulation size desired and hence the amount of botulinum toxin, a suitable amount of the microspheres can be compressed at about 8000 p.s.i. for 5 seconds or at 3000 p.s.i. for 17 seconds in a mold to form oral formulation discs encapsulating the neurotoxin. Thus, the microspheres can be compression molded pressed into discs 1.4 cm in diameter and 1.0 mm thick, packaged in aluminum foil pouches under nitrogen atmosphere and sterilized by $2.2 \times 10^4$ Gy gamma irradiation.

Example 5

Water In Oil Method For Making a Biodegradable Botulinum Toxin Oral Formulation

A botulinum toxin oral formulation can be made by dissolving a 80:20 copolymers of polyglycolic acid and the polylactic acid can in 10% w/v of dichloromethane at room temperature with gentle agitation. A water-in-oil type emulsion can then be made by adding 88 parts of the polymer solution to 1 part of a 1:5 mixture of Tween 80 (polyoxyethylene 20 sorbitan monooleate, available from Acros Organics N.V., Fairlawn, N.J.) and Span 85 (sorbitan trioleate) and 11 parts of an aqueous mixture of 75 units of BOTOX® (botulinum toxin type A complex) and Quil A (adjuvant). The mixture is agitated using a high-speed blender and then immediately spray-dried using a Drytec Compact Laboratory Spray Dryer equipped with a 60/100/120 nozzle at an atomizing pressure of 15 psi and an inlet temperature of 65 degrees C. The resultant microspheres have a diameter of about 20 μm diameter and are collected as a free-flowing powder. Traces of remaining organic solvent are removed by vacuum evaporation.

Example 6

Reduced Temperature Method For a Biodegradable Botulinum Toxin Oral Formulation

A botulinum toxin oral formulation can be made at a low temperature so as to inhibit toxin denaturation as follows. 0.3 g of PLGA/ml of methylene chloride or ethyl acetate is mixed with 0.1 ml of neurotoxin solution/ml of the polymer-organic solution at a reduced temperature (2-8 degrees C.). A first set of botulinum toxin incorporating microspheres made, as set forth in Example 1 (the polymer solution is formed by dissolving the polymer in methylene chloride), from a 75:25 lactide:glycolide polymer with an inherent viscosity (dL/g) of about 0.62 (available form MTI) and can degrade in a patient's GI tract.

Compositions and methods according to the invention disclosed herein has many advantages, including the following:

1. a single oral formulation can be used to provide therapeutically effective continuous or administration of a neurotoxin over a period of one year or longer.

2. the neurotoxin is delivered to a localized tissue area without a significant amount of neurotoxin appearing systemically.

3. reduced need for patient follow up care.

4. reduced need for periodic injections of neurotoxin to treat a condition, such as a neuromuscular disorder.

5. increased patent comfort due to no injections being required.

6. improved patient compliance.

An advantage of the present oral formulations for neurotoxins include rapid delivery of consistent therapeutic levels of neurotoxin to the GI target tissue. The advantages also include increased patient compliance and acceptance.

All references, articles, publications and patents and patent applications cited herein are incorporated by reference in their entireties.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes oral formulations where two or more botulinum toxins, are administered concurrently or consecutively via the oral formulation. For example, botulinum toxin type A can be administered via an oral formulation until a loss of clinical response or neutralizing antibodies develop, followed by administration also by suitable oral formulation of a botulinum toxin type B or E. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin via oral formulation so as to provide an adjunct effect such as enhanced or a more rapid onset of denervation before the neurotoxin, such as a botulinum toxin, begins to exert its therapeutic effect.

The present invention also includes within its scope the use of a neurotoxin, such as a botulinum toxin, in the preparation of an oral formulation medicament, for the treatment of a GI disorder.

Accordingly, the spirit and scope of the following claims should not be limited to the descriptions of the preferred embodiments set forth above.

I claim:

1. A solid form botulinum toxin oral formulation for the treatment of a gastrointestinal disorder in a human patient, comprising:

an effective amount of a botulinum toxin type A, encapsulated in a carrier, thereby forming a botulinum toxin oral formulation, wherein the carrier is formulated to release the botulinum toxin type A in a gastrointestinal tract of the human patient without a significant immune system response, wherein a controlled gastric retention of the solid form can be achieved by a method selected from the group consisting of mucoadhesion, flotation, sedimentation, expansion, or by a simultaneous administration of pharmacological agents which delay gastric emptying, and wherein the effective amount of the botulinum toxin type a is determined relative to the patient's weight and ranging between 0.01 units/kg and about 25 units/kg.

2. The oral formulation of claim 1, wherein the carrier comprises a plurality of polymeric microspheres.

3. The oral formulation of claim 1, wherein the carrier comprises a polymeric matrix.

* * * * *